(12) United States Patent
Knor (10) Patent No.: US 9,155,853 B2
(45) Date of Patent: Oct. 13, 2015

(54) SYSTEMS AND METHODS OF ADJUSTING VENTILATOR MODES AND SETTINGS VISUALLY VIA A TOUCHSCREEN

(75) Inventor: Timothy Michael Knor, Madison, WI (US)

(73) Assignee: General Electric Company, Schenectady, NY (US)

(*) Notice: Subject to any disclaimer, the term of this patent is extended or adjusted under 35 U.S.C. 154(b) by 697 days.

(21) Appl. No.: 13/222,368

(22) Filed: Aug. 31, 2011

(65) Prior Publication Data

US 2013/0055134 A1   Feb. 28, 2013

(51) Int. Cl.
*A61M 16/00*   (2006.01)

(52) U.S. Cl.
CPC ....... *A61M 16/0051* (2013.01); *A61M 16/0057* (2013.01); *A61M 2016/0027* (2013.01); *A61M 2016/0033* (2013.01); *A61M 2205/505* (2013.01)

(58) Field of Classification Search
CPC .................. A61M 2205/505; A61M 16/0057; A61M 16/0051
USPC ......................................................... 715/771
See application file for complete search history.

(56) References Cited

U.S. PATENT DOCUMENTS

| | | | | |
|---|---|---|---|---|
| 5,494,028 | A * | 2/1996 | DeVries et al. | 128/205.24 |
| 5,598,838 | A * | 2/1997 | Servidio et al. | 128/204.23 |
| 5,931,160 | A * | 8/1999 | Gilmore et al. | 128/204.21 |
| 6,463,930 | B2 * | 10/2002 | Biondi et al. | 128/204.21 |
| D638,852 | S * | 5/2011 | Skidmore et al. | D14/488 |
| 8,001,967 | B2 * | 8/2011 | Wallace et al. | 128/204.21 |
| 8,021,310 | B2 * | 9/2011 | Sanborn et al. | 600/538 |
| D649,157 | S * | 11/2011 | Skidmore et al. | D14/492 |
| 8,335,992 | B2 * | 12/2012 | Skidmore et al. | 715/771 |
| 8,408,203 | B2 * | 4/2013 | Tham et al. | 128/204.21 |
| 8,443,294 | B2 * | 5/2013 | Skidmore et al. | 715/764 |
| 8,453,645 | B2 * | 6/2013 | Figueiredo et al. | 128/204.23 |
| 8,499,252 | B2 * | 7/2013 | Skidmore | 715/777 |
| 8,555,881 | B2 * | 10/2013 | Wallace et al. | 128/204.21 |
| 8,555,882 | B2 * | 10/2013 | Wallace et al. | 128/204.21 |
| 2001/0004893 | A1 * | 6/2001 | Biondi et al. | 128/204.18 |
| 2001/0035186 | A1 * | 11/2001 | Hill | 128/204.18 |
| 2003/0045807 | A1 * | 3/2003 | Daniels et al. | 600/538 |
| 2004/0118404 | A1 * | 6/2004 | Wallace et al. | 128/205.23 |
| 2007/0163584 | A1 * | 7/2007 | Bohm et al. | 128/204.18 |
| 2008/0072896 | A1 * | 3/2008 | Setzer et al. | 128/200.24 |
| 2008/0185009 | A1 | 8/2008 | Choncholas et al. | |
| 2009/0293876 | A1 * | 12/2009 | Soliman et al. | 128/204.22 |
| 2009/0301492 | A1 * | 12/2009 | Wysocki et al. | 128/204.23 |
| 2010/0234705 | A1 * | 9/2010 | Lynn | 600/324 |
| 2012/0000470 | A1 * | 1/2012 | Milne et al. | 128/205.23 |
| 2012/0125337 | A1 * | 5/2012 | Asanoi | 128/204.23 |
| 2012/0145152 | A1 * | 6/2012 | Lain et al. | 128/204.23 |
| 2012/0204875 | A1 * | 8/2012 | Brazy et al. | 128/204.22 |

(Continued)

*Primary Examiner* — William Bashore
*Assistant Examiner* — Nathan Shrewsbury
(74) *Attorney, Agent, or Firm* — Andrus Intellectual Property Law, LLP (57) ABSTRACT

The systems and methods of the present application provides a graphical user interface (GUI) for adjusting the modes and settings of a patient ventilator. Upon selecting the type of breath setting (mechanical and/or pressure supported), and the target and control parameters for each breath setting, an ideal set of pressure, flow and volume waveforms are displayed on a touch-screen GUI. The user is then able to adjust any of the waveforms using the touch-screen GUI to the desired ventilator settings for that particular patient. The user then confirms the settings and the ventilator operates according to the user-set waveforms.

20 Claims, 6 Drawing Sheets

(56) References Cited

U.S. PATENT DOCUMENTS

| | | | |
|---|---|---|---|
| 2012/0216809 A1* | 8/2012 | Milne et al. | 128/204.18 |
| 2012/0302845 A1* | 11/2012 | Lynn et al. | 600/323 |
| 2013/0060110 A1* | 3/2013 | Lynn et al. | 600/324 |
| 2013/0283197 A1* | 10/2013 | Skidmore | 715/771 |
| 2014/0228905 A1* | 8/2014 | Bolea | 607/42 |
| 2014/0351738 A1* | 11/2014 | Kokovidis et al. | 715/771 |

* cited by examiner

SYSTEMS AND METHODS OF ADJUSTING VENTILATOR MODES AND SETTINGS VISUALLY VIA A TOUCHSCREEN

FIELD

The present application is directed to the field of patient ventilation. More specifically, the present application is directed to the field of user interfaces and systems for adjusting ventilator settings.

BACKGROUND

Current medical ventilators used in the operating room, intensive care unit, and home markets have many different ventilation modes. For example, volume control, pressure control, etc. modes are used to deliver therapy to a patient. These modes have many different names and settings, depending on the model and manufacturer, that can be confusing to the clinician. In such ventilators, the user cannot visually see what it is they are setting, but are merely setting a number for a particular mode. Currently, a user cannot touch a waveform on the ventilator screen and draw what it is they want to be delivered to the patient. In current ventilators, the user needs to remember what the name of the mode they were using. A user cannot currently decide what type of breath (mechanical or pressure support) is to be delivered to the patient and draw it out on the screen of the ventilator. With users of ventilators and other medical devices becoming more familiar and comfortable with touchscreens, a method of setting up ventilation settings via touchscreen is needed, and would be easier and more effective than some current confusing terminologies that the user must learn for current ventilator mode settings.

SUMMARY

The systems and methods of the present application provides a graphical user interface (GUI) for adjusting the modes and settings of a patient ventilator. Upon selecting the type of breath setting (mechanical and/or pressure supported), and the target and control parameters for each breath setting, an ideal set of pressure, flow and volume waveforms are displayed on a touch-screen GUI. The user is then able to adjust any of the waveforms using the touch-screen GUI to the desired ventilator settings for that particular patient. The user then confirms the settings and the ventilator operates according to the user-set waveforms.

In one embodiment of the present application, a ventilator system comprises a ventilator operative to provide patient with ventilation, a ventilator display operative to provide a graphical user interface (GUI) wherein the GUI includes a touchscreen, and a processor programmed to: receive a selection for any of a mechanical or PSV breath setting from the touchscreen; receive a selection for a target parameter and a control parameter for each of the mechanical or PSV breaths from the touchscreen, display on the ventilator display a set of ideal waveforms corresponding to the selected breath setting, target parameter and control parameter, adjust the set of ideal waveforms in response to altering any of the set of ideal waveforms with the touchscreen to a desired patient setting, and set the ventilator according to the desired patient settings.

In another embodiment of the present application, a computerized method of adjusting a ventilator visually, comprises providing a graphical user interface (GUI) on a ventilator display, selecting any of a mechanical breath or a PSV breath setting using the GUI, selecting a target parameter and a control parameter for each of the breath settings with the GUI, displaying a set of ideal waveforms on the GUI, adjusting any of the set of ideal waveforms with the GUI to a desired patient setting, and setting the ventilator with the GUI according to the desired patient setting.

In another embodiment of the present application, in a ventilator system having a graphical user interface embodied on a ventilator display, a method of adjusting a ventilator visually, the method comprising selecting any of a mechanical breath or PSV breath setting, selecting a target parameter and a control parameter for each of the breath settings, displaying a set of ideal waveforms, adjusting any of the set of ideal waveforms to a desired patient setting, and setting the ventilator according to the desired patient setting.

DETAILED DESCRIPTION

In the present description, certain terms have been used for brevity, clearness and understanding. No unnecessary limitations are to be applied therefrom beyond the requirement of the prior art because such terms are used for descriptive purposes only and are intended to be broadly construed. The different systems and methods described herein may be used alone or in combination with other systems and methods. Various equivalents, alternatives and modifications are possible within the scope of the appended claims. Each limitation in the appended claims is intended to invoke interpretation under 35 U.S.C. §112, sixth paragraph, only if the terms "means for" or "step for" are explicitly recited in the respective limitation.

Figure 1:
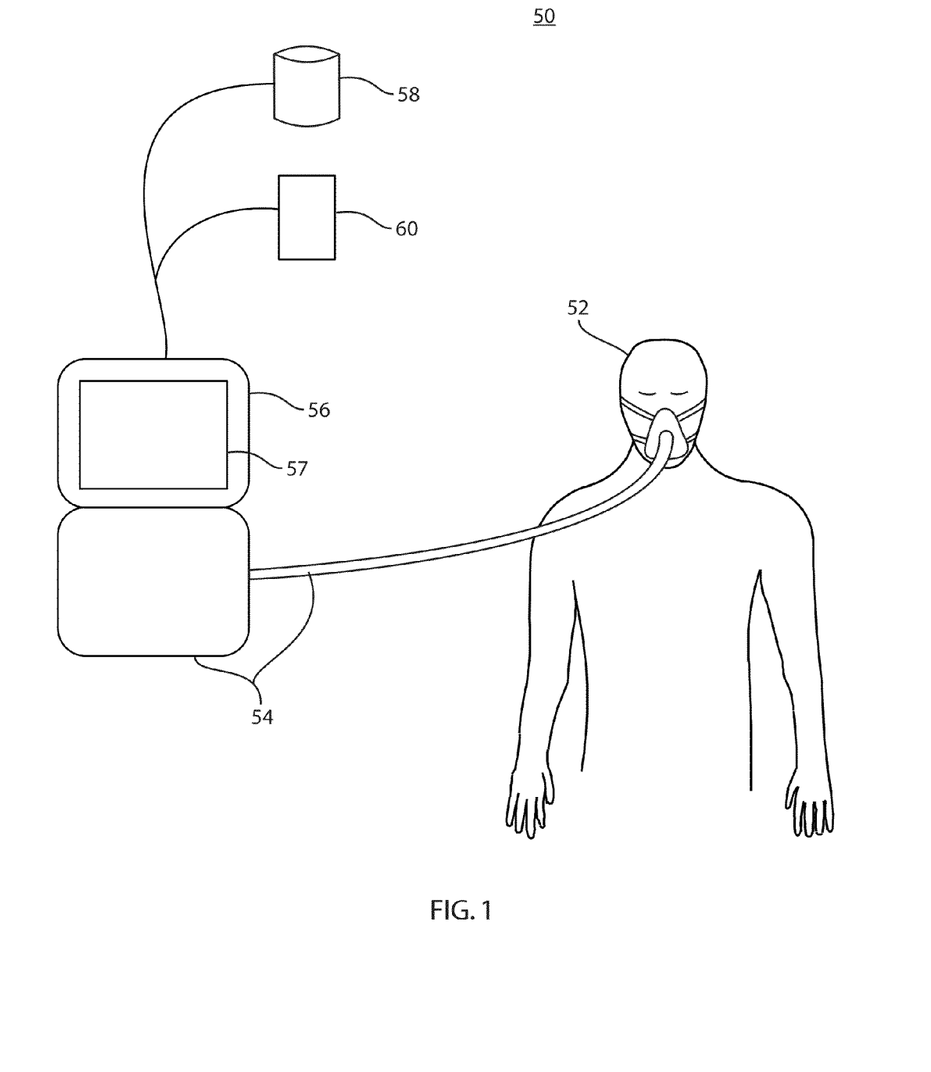
FIG. 1 is a schematic diagram illustrating an embodiment of a patient ventilator system including a ventilator display of the present application.

FIG. 1 illustrates a schematic diagram illustrating a ventilator system 50 used in the present application. Here, the patient ventilator system 50 is treating a patient 52, wherein a ventilator 54 and a ventilator monitor 56 having a graphical user interface 57 allows a user to set various settings on the ventilator 54 for proper treatment of the patient 52. It should be noted that the patient ventilator system 50 here shows a non-invasive system including a mask for delivering ventilation to the patient 52. It should be understood that the patient ventilator system 50 of the present application could also include an invasive delivery device, such as an intubation device. The patient ventilator system 50 further alternatively includes a storage medium 58 and a processor 60 that may be in a separate computing device (not shown), or integrated within the ventilator 54 and/or the ventilator monitor 56. The system and method described herein include a set of computer executable code that is stored in the storage medium 58 and processed by the processor 60 in order to effectuate the system and method of adjusting ventilator modes and settings visually via a touch screen by implementing a graphical user interface 57 on the ventilator display 56.

Figure 2:
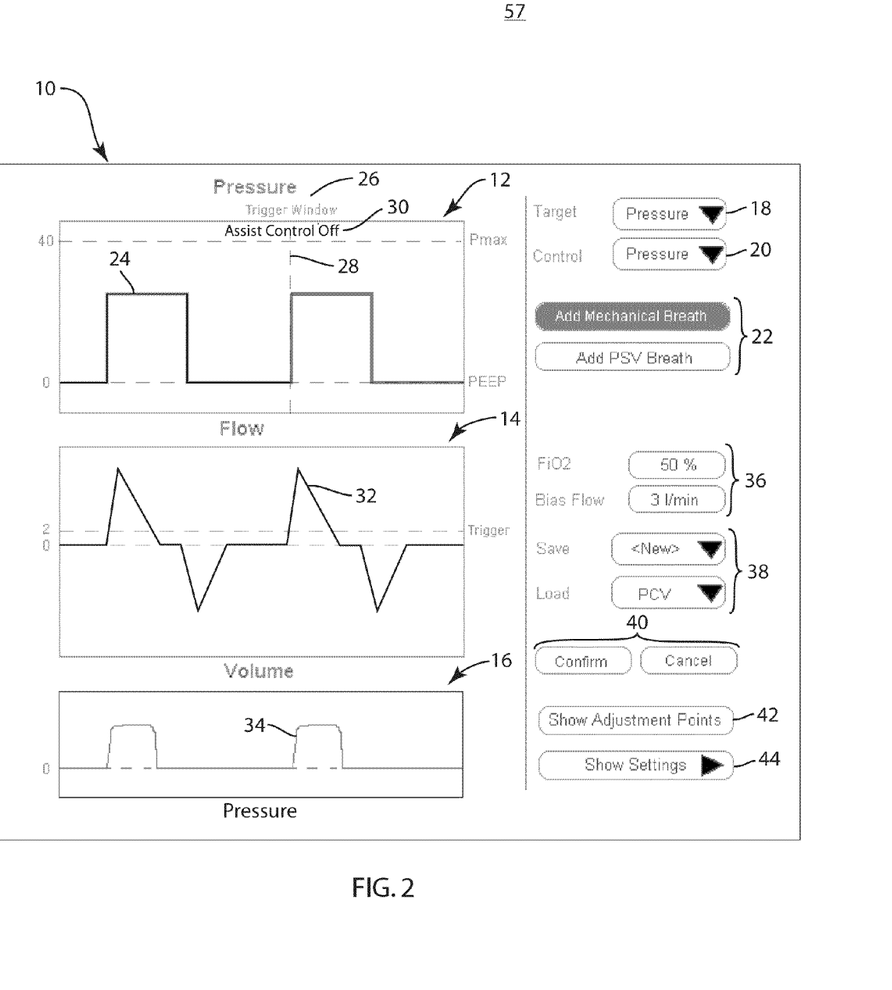
FIG. 2 is a graphical representation illustrating an embodiment of a graphical user interface (GUI) of a ventilator display of the present application.

Referring to FIG. 2, the modes screen 10 is displayed on the ventilator monitor 56 when the user opens a modes menu for adjusting the ventilator settings for the patient 52. It should be noted that the precise configuration of the modes screen 10 in FIG. 2 is exemplary, in that the display areas 12, 14, 16, and the various selectors illustrated to the right of the display areas 12, 14, 16, may be interchanged or configured according to a user preference.

Referring to FIG. 2, when a user wishes to change a ventilation mode on a ventilator 54, the user opens a modes menu which will display a modes screen 10 having three (3) graphical areas (pressure, flow, and volume) 12, 14, 16, which correspond to the waveforms the user commonly uses. The user will then decide what type of breath they want administered to the patient 52, mechanical (mandatory breaths) or pressure supported ventilation (PSV) breaths (spontaneous breaths triggered by the patient) administered to the patient 52 using the breath type selector 22. The breath has two additional parameters the user must specify, the target (pressure or volume) using the target selector 18 and the control type (pressure or flow) using the control selector 20, as this determines how the breath is to be delivered to the patient 52. As an example, the user may select a mechanical breath with the target to be pressure and the control to be pressure. The waveforms 24, 32, 34 currently displayed in the screen 10 would then be updated to show the ideal waveforms 24, 32, 34 for this type of breath. Alternatively, if the patient has been ventilated for some time and patient ventilator data exists, then the ideal waveforms may be adjusted to reflect this patient ventilator data. The user may then touch and adjust various parts of the waveform 24, 32, 34 at adjustment points 62 to change various settings, which will be discussed in further detail below. For example, the user may drag the top of a pressure waveform 24 up or down to increase or decrease the Pinsp (Inspirational Pressure) setting or the user may drag the right edge of the pressure waveform 24 left or right to decrease or increase the Tinsp (Inspirational Time) setting. Dragging the center of a mechanical breath left or right may increase or decrease the respiratory rate. The waveforms 24, 32, 34 will update as necessary to match the proposed setting as drawn by the user.

As discussed above, a user may select a mechanical or PSV breath, and then set the target and control parameters by pressure or flow. Therefore, there are four (4) combinations for each type of breath (mechanical and PSV) for Target and Control as follows in Table 1:

TABLE 1

| ID | Target | Control |
|---|---|---|
| 1 | Pressure | Pressure |
| 2 | Pressure | Flow |
| 3 | Volume | Pressure |
| 4 | Volume | Flow |

While all four (4) combinations are physically possible for both mechanical and pressure supported breaths, not all may be used in current ventilators 54.

Referring again to FIG. 2, the target and control selectors 18, 20 may be used to configure the target and control of the breath. In another embodiment, the user may press "Add Mechanical Breath" breath type selector 22, and a box would appear (not shown) giving the user a list of choices of the types of mechanical breaths they wish to add similarly configured for pressure supported breaths. In another embodiment, once the breath is added, the breath type selector 22 may change to read "remove mechanical breath" or "remove PSV breath".

Still referring to FIG. 2, the modes screen 10 also includes various parameter indicators 36. Here, the parameter indicators show level of FiO2, as well as a bias flow for the particular patient being monitored. Furthermore, the modes screen 10 includes save/load selectors 38 for managing the display areas 12, 14, 16 of the modes screen 10. Here, the save/load selectors 38 include a save selector that allows the user to save a particular set of waveforms 24, 32, 34, created by the user, and name the saved set of waveforms to their preference and choosing and the load selector allows the user to load a previously saved set of waveforms 24, 32, 34 setting that they previously saved, or one provided by the manufacturer. Still referring to FIG. 2, when a user calls up the modes screen 10, and ideal waveforms 24, 32, 34 appear for the patient 52, a user may alter the waveforms 24, 32, 34 in order to change the ventilator 54 settings for the patient 52. However, the ventilator 54 will not deliver the changed settings to the patient 52 until the user confirms the settings. The confirm/cancel selectors 40 allow a user to either confirm or cancel the changed settings of the waveforms 24, 32, 34 prior to the ventilator 54 changing the settings delivered to the patient 52. Alternatively, when a user is adjusting waveforms 24, 32, 34 that are not newly added waveforms 24, 32, 34, that is, waveforms 24, 32, 34 that have already been confirmed once, a confirm will not be required to set the ventilator 54 according to changes made to the waveforms.

FIG. 3a-17 are exemplary images of various display areas 12, 14, 16 and waveforms 24, 32, 34 and how the waveforms 24, 32, 34 may be adjusted by the user with a touchscreen. As stated previously, these figures include examples, and there may be other ways to use gestures or strokes on a touchscreen to manipulate the waveforms 24, 32, 34 to adjust the ventilator settings. Furthermore, for some of the waveforms 24, 32, 34, an additional "before/after" view was included. Again, this was done for exemplary purposes only, and should limit the scope of the appended claims. May of the figures illustrate an arrow pointing in two (2) directions indicating the direction of possible adjustment of that adjustment point 62. However, there may be times where the user won't be allowed to go one direction or another, according to any possible medical rules. In other words, the ventilator 54 may restrict the settings as it sees fit.

Figure 3A:
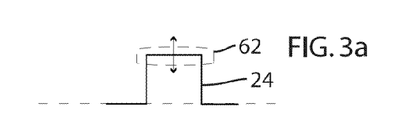
FIGS. 3a-3b are graphical representations illustrating an embodiment of pressure and volume display areas, respectively, of a graphical user interface (GUI) of a ventilator display of the present application.

Referring to FIG. 3a, in a pressure targeted breath, the inspiratory pressure is the peak pressure delivered to the patient. In some systems, inspiratory pressure may go by different names: if it is a mechanical breath, Pinsp, or pressure supported breath, Psupp, but the measure is the same. In FIG. 3a, the inspiratory pressure is the top horizontal line of the pressure waveform 24. A method of adjusting this graphically is to touch this top pressure line in the graph anywhere on the adjustment point 62 and drag it up or down to the desired level (in the direction of the arrows).

Figure 3B:
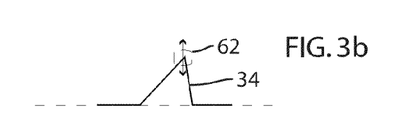

Referring to FIG. 3b, in a volume targeted breath, the tidal volume setting determines the target volume to be delivered to the patient. A method of adjusting this graphically is to touch the top of the volume waveform 34 (its peak volume) at the adjustment point 62 and drag the adjustment point 62 up or down in the direction of the arrows to the desired level.

Figure 4A:
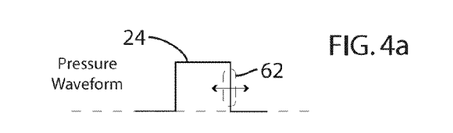
FIGS. 4a-4b are graphical representations illustrating an embodiment of pressure and flow display areas, respectively, of a graphical user interface (GUI) of a ventilator display of the present application.
Figures 4B, 5A:
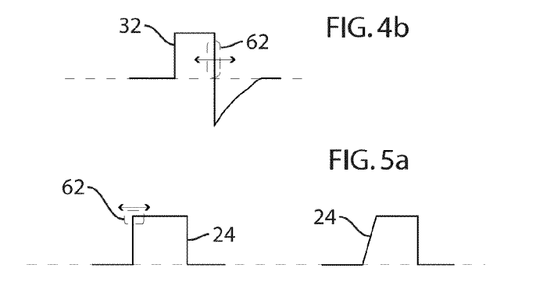
FIGS. 5a-5b are graphical representations illustrating an embodiment of pressure and flow display areas, respectively, of a graphical user interface (GUI) of a ventilator display of the present application.

Referring to FIGS. 4a and 4b, for mechanical breaths, the inspiratory time (the width of the square waveform 24, 32) determines how long the ventilator 54 should deliver the mechanical breath to the patient 52. This may be adjusted on the pressure waveform 24 for pressure controlled breaths by dragging the right edge adjustment point 62 left or right. Similarly for flow controlled breaths, dragging the right edge adjustment point 62 of the flow waveform 32 left or right.

Referring to FIG. 5a, for pressure controlled breaths (either mechanical or PSV), there is a rise time setting that determines how fast the system attempts to reach its peak. This is adjusted by changing the slope of the left edge of the pressure waveform 24 by dragging the upper-left corner adjustment point 62 left or right. The before and after waveform 24 in FIG. 5a illustrates how moving the adjustment point 62 to the right in this case increases the rise of time of the pressure waveform 24.

Figure 5B:
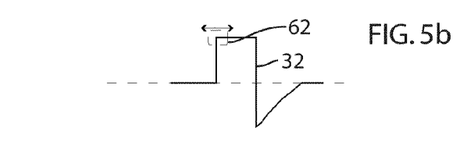

Referring to FIG. 5b, similarly as adjusting the rise time for pressure controlled breaths (either mechanical or PSV), adjusting the rise time of a flow controlled breath is done by changing the slope of the left edge of the flow waveform 32 by dragging the upper-left corner adjustment point 62 left or right.

Figure 6A:
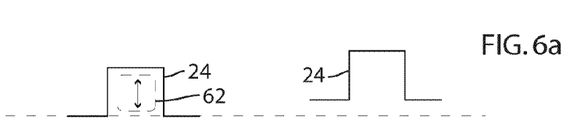
FIGS. 6a-6b are graphical representations illustrating an embodiment of pressure display areas, respectively, of a graphical user interface (GUI) of a ventilator display of the present application.
Figure 6B:
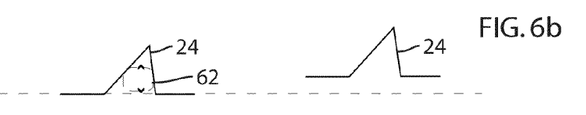

Referring to FIGS. 6a and 6b, PEEP is the baseline pressure delivered to the patient 52 at all times, even when not delivering a mechanical or pressure supported breath. This may be adjusted in two (2) ways depending on whether the user wants to keep the height of the pressure waveform 24 the same, or whether the user wants to adjust both the baseline PEEP value and the relative height of the pressure waveform 24. In FIGS. 6a and 6b, the user drags the adjustment point 62 in the center of the breath on the pressure waveform 24 up or down to move the waveform 24 up or down and keep the height of the waveform 24 the same.

Figure 7:
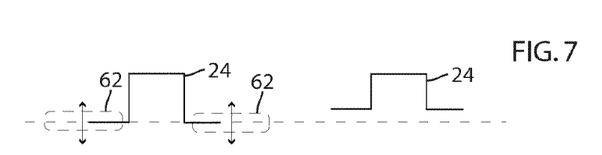
FIG. 7 is a graphical representation illustrating an embodiment of a pressure display area of a graphical user interface (GUI) of a ventilator display of the present application.

The version of adjusting PEEP in FIG. 7 only applies to mechanical pressure targeted breaths, and allows the user to adjust the PEEP level while keeping the peak pressure at a current level. This is adjusted by dragging the baseline pressure (PEEP) up or down at the adjustment point 62.

Figure 8A:
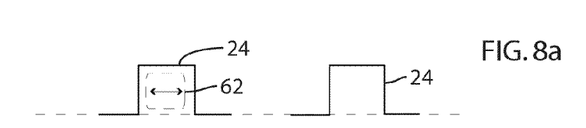
FIGS. 8a-8b are graphical representations illustrating an embodiment of pressure and volume display areas, respectively, of a graphical user interface (GUI) of a ventilator display of the present application.
Figure 8B:
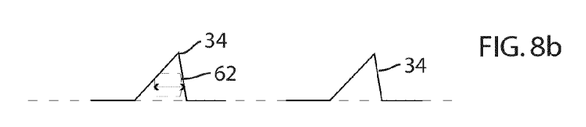

Referring to FIGS. 8a and 8b, the mechanical breath rate (also called frequency in some systems) is the rate of delivery of mechanical breaths, i.e. 12 bpm means 12 breaths per minute. This may be adjusted by dragging one of the mechanical breaths in the pressure or volume waveform 24, 34 by the adjustment point 62 left or right to adjust the difference between the adjusted breath and the next breath. In the example of FIGS. 8a and 8b, the left breath is adjusted, the right breath stays. In essence, the expiratory time is adjusted by increasing or decreasing the time the ventilator is not delivering a breath. By adjusting the inspiratory time and expiratory time, the breath rate to the patient is adjusted.

Figure 9:
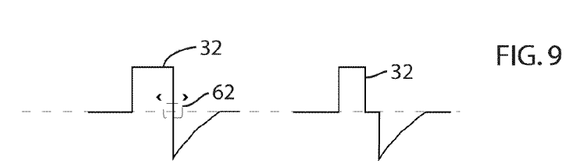
FIG. 9 is a graphical representation illustrating an embodiment of a flow display area of a graphical user interface (GUI) of a ventilator display of the present application.

Referring to FIG. 9, the inspiratory pause time is the time during the inspiratory phase of the breath that the ventilator stops flowing gas to the patient 52. This is adjusted by dragging the bottom-right corner adjustment point 62 of the inspiratory portion of the breath on the flow waveform 32 left or right. The inspiratory time remains the same, so the width of the peak of the flow waveform 32 could shrink, as shown in the "after" waveform 32.

Figure 10A:
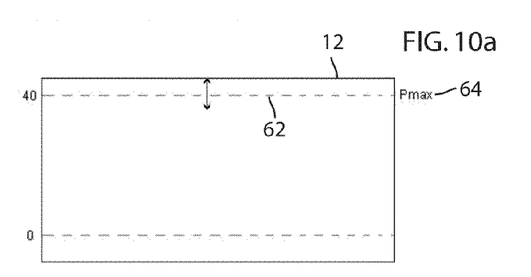
FIGS. 10a-10b are graphical representations illustrating an embodiment of pressure display areas of a graphical user interface (GUI) of a ventilator display of the present application.

Referring to FIG. 10a, all ventilators have an absolute maximum pressure allowed to be delivered to the patient regardless of the type of breath. In some systems, this is referred to as Pmax 64. In some systems, this is a dotted line across the pressure display 12 that may be dragged up or down by the adjustment point to set the maximum pressure value 64. The label "Pmax" could also include an adjustment point 62 and be dragged up or down as well.

Figure 10B:
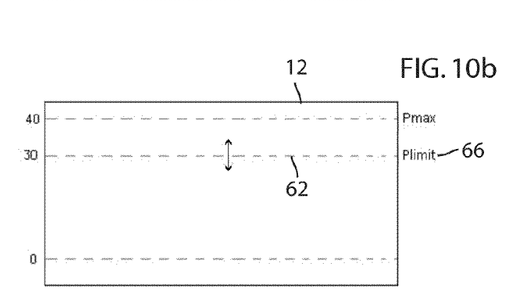

Referring to FIG. 10b, similar to the maximum pressure for all breaths in FIG. 10a, there is a setting exclusively for volume controlled breaths, sometimes called Plimit 66, that is a soft limit for the pressure of a volume breath. The ventilator 54 reacts differently when it reaches this limit than the Pmax limit. Adjusting Plimit 66 is similar to adjusting Pmax 64, by adjusting an adjustment point 62 on a dotted line labeled Plimit 66 that can be dragged up or down to set the desired value.

Figure 11:
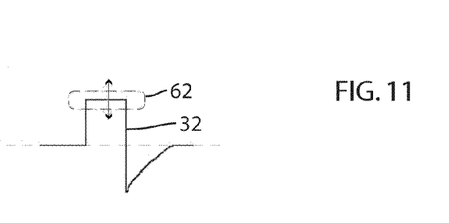
FIG. 11 is a graphical representation illustrating an embodiment of a flow display area of a graphical user interface (GUI) of a ventilator display of the present application.

Referring to FIG. 11, some flow controlled modes allows the user to set the approximate flow to be delivered to the patient 52. This is adjusted by dragging the peak flow level of the flow waveform 32 at the adjustment point 62.

Figure 12A:
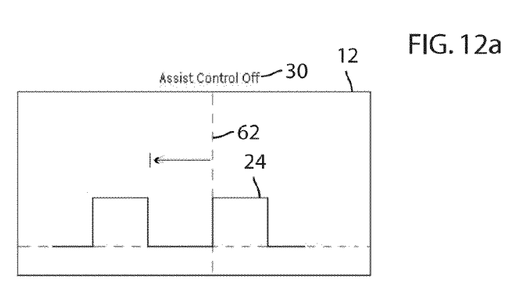
FIGS. 12a-12b are graphical representations illustrating an embodiment of pressure display areas of a graphical user interface (GUI) of a ventilator display of the present application.
Figure 12B:
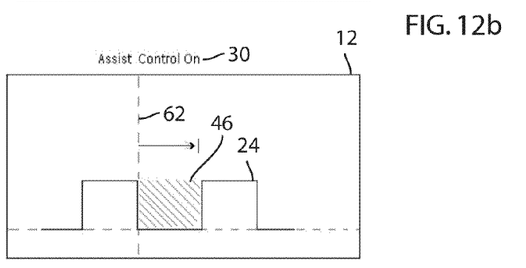

Referring to FIGS. 12a and 12b, for ventilation modes that have only mechanical breaths (and no PSV breaths), the user may turn on or off a setting called Assist Control by selecting the assist control Selector 30. This setting allows modes with mechanical only breaths to deliver the mechanical breath early if a patient 52 initiated trigger condition occurs. Assist control may be adjusted by dragging the vertical dotted line adjustment point 62 left or right, snapping from the left edge of the right breath to the right edge of the left breath and cannot be left in between breaths, as shown in FIGS. 12a and 12b, respectively. The shaded area in FIG. 12b illustrates an area where a patient trigger would deliver the mechanical breath, or patient trigger area 46. In other embodiments, there could be other ways of visualizing this region, but showing the patient trigger area 46 to the user reinforces how that setting works.

Figure 13:
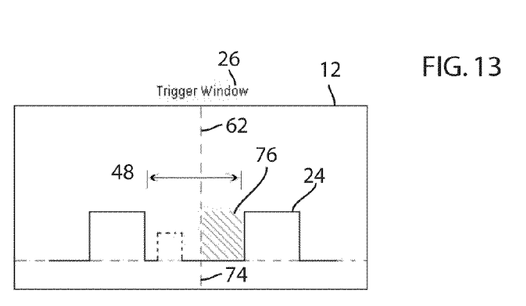
FIG. 13 is a graphical representation illustrating an embodiment of a pressure display area of a graphical user interface (GUI) of a ventilator display of the present application.

Referring to FIG. 13, the trigger window setting only applies for modes that have both mechanical breaths and pressure supported breaths. This setting is similar to assist control, but can be adjusted in between breaths as shown. In FIG. 13, the small black dotted square wave is a PSV breath 48. It is visualized as a dotted waveform because this can occur anywhere between the left edge of the trigger window 74 and the right edge of the previous breath, depending on when the patient 52 triggers the breath. If the patient 52 triggers a breath in the shaded region on the right side of the trigger window 74 in the trigger window area 76, then the ventilator 54 will deliver the next mechanical breath immediately. The trigger window 74 can be adjusted by dragging the vertical dotted adjustment point 62 line left or right, or the trigger window indicator 26 may also be dragged to adjust the trigger window 74, and the trigger window area 76 would adjust as the user drags the trigger window.

The two settings discussed in FIGS. 12a, 12b and 13, trigger window 74 and assist control, are confusing to users. By showing how the setting affects the window visually as shown above, it should help users decide how to set these settings for their patient 52.

Figure 14:
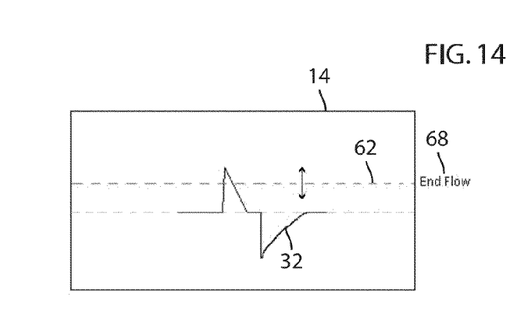
FIG. 14 is a graphical representation illustrating an embodiment of a flow display area of a graphical user interface (GUI) of a ventilator display of the present application.

Referring now to FIG. 14, end flow 68 is a percentage of the peak flow during a PSV Breath that should trigger the end of the PSV breath. The end flow threshold 68 may be adjusted graphically by a horizontal dotted line adjustment point 62 that can be dragged up or down from the peak of the flow waveform 32 in a flow display area 14.

Figure 15:
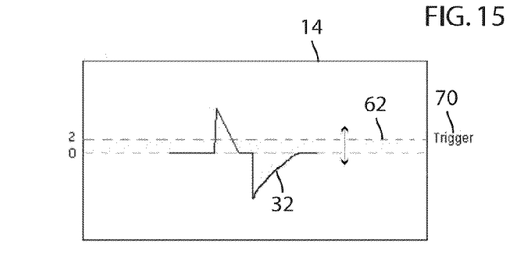
FIG. 15 is a graphical representation illustrating an embodiment of a flow display area of a graphical user interface (GUI) of a ventilator display of the present application.

Referring to FIG. 15, flow trigger 70 is the level of flow required by the patient 52 to indicate the patient 52 initiated effort for a breath. Usually this "triggers" a breath, either PSV or mechanical, by the ventilator 54. In a flow display area 14, the flow trigger 70 may be adjusted by adjusting a horizontal dotted line adjustment point 62 up or down on the flow waveform 32.

Figure 16:
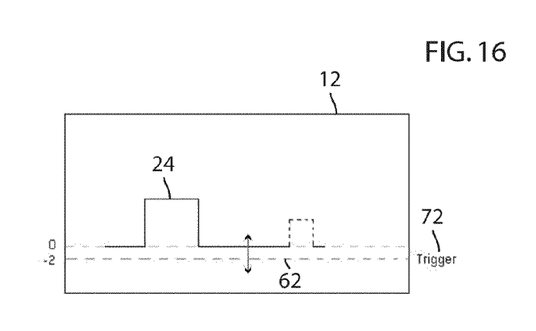
FIG. 16 is a graphical representation illustrating an embodiment of a pressure display area of a graphical user interface (GUI) of a ventilator display of the present application.

Referring to FIG. 16, similar to the flow trigger 70, pressure trigger 72 setting is the amount of pressure below PEEP the patient 52 needs to draw in order to indicate patient effort. Usually this "triggers" a breath, either PSV or mechanical by the ventilator 54. In a pressure display area 12, the pressure trigger threshold 32 may be adjusted by adjusting a horizontal dotted line adjustment point 62 up or down on the pressure waveform 24.

Figure 17A:
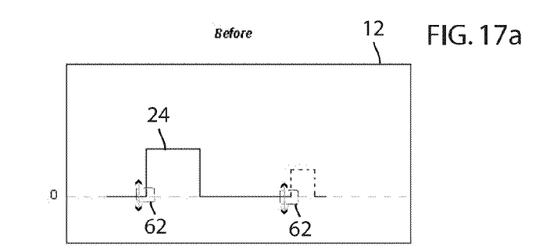
FIGS. 17a-b are graphical representations illustrating an embodiment of pressure display areas of a graphical user interface (GUI) of a ventilator display of the present application.
Figure 17B:
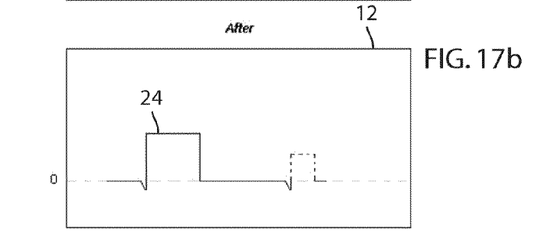

Referring to FIGS. 17a and 17b, in an alternative embodiment, the pressure trigger 72 is adjusted by adjusting the lower-left corner of the inspiratory portion of the breath up or down with an adjustment point 62. This would create a dip at that point 62. This mimics closer to what physically happens when a patient exerts effort (drawing negative pressure). Adjusting either the mechanical or PSV breath's pressure trigger 72 in this fashion would automatically change the other, i.e., adjusting one automatically has the other breath use the same setting.

In any of the above-described actions, when the user is adjusting one of the adjustment points 26, the display area 12, 14, 16 updates with feedback to the user, which can include updating the other display areas 12, 14, 16 as appropriate, calculated values for other related settings. For example, as the Rate or Tinsp is being adjusted, the I:E ratio can be calculated and displayed. Any constraints on why a setting cannot be changed any further, e.g., when some settings are not feasible, and a message to the user can be displayed to explain why this is and what action they can take.

In some cases, it may not be obvious to the user what parts of the waveforms 24, 32, 34 are adjustment points 62. To see all the adjustment points on the modes screen 10, the user may touch the show adjustment points selector 42 (FIG. 2) to show what areas have adjustment points 62 and in some embodiments, a help diagram or notes to illustrate what the setting is and directions for adjustment. Also, some users may not be fully comfortable with only having graphically adjustable ventilation modes, and they may wish to see and set settings numerically while seeing how the waveforms adjusts to those settings. In this case, the user may touch the show settings selector 44 to see and set the settings numerically (FIG. 2).

Figure 18:
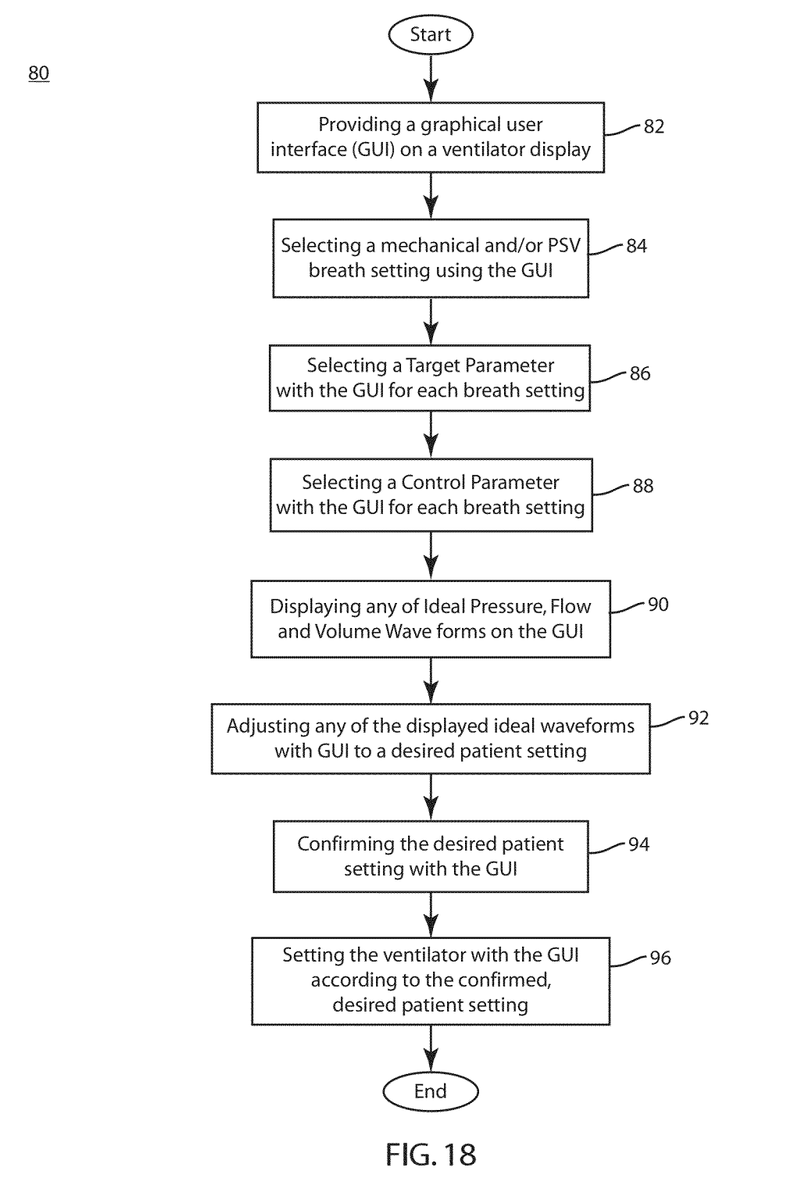
FIG. 18 is a flowchart illustrating an embodiment of a method of the present application.

Referring now to FIG. 18, a method 80 of adjusting ventilator modes and settings visually via touch screen is illustrated. Here, in step 82, a graphical user interface 57 is provided for a user on a ventilator display. As discussed above, this ventilator display allows a user to see the particular waveforms representing flow, pressure and volume that are being administered to the patient. The graphical user interface 57 also includes a number of selectors and indicators that illustrate for the user and allow the user to see and adjust all of the particular settings. In step 84, the user selects a mechanical and/or PSV breath setting to control and set on the ventilator for the patient using the GUI 57. In step 86, the user utilizes a target selector to select a target parameter for each selected breath, and in step 88, the user utilizes a control selector to select a control parameter for each breath with the GUI 57. Once the target parameter and control parameter are selected in steps 86 and 88, respectively, the GUI 57 displays ideal pressure, flow and volume waveforms on the GUI 57 in step 90. These ideal waveforms are representative of known ideal waveforms for the combination of selections made in steps 84-88.

Still referring to FIG. 18, in step 92, the user utilizes the GUI 57 to adjust any of the displayed ideal waveforms to a desired patient setting. The user may use various adjustment points as described above in FIGS. 2-17b in order to adjust various settings on any of the ideal waveforms. In step 94, the patient confirms the adjustments made to the ideal waveforms as desired patient settings by utilizing such a selector on the GUI 57, and in step 96, this confirmation allows the GUI 57 to set the ventilator according to the confirmed, desired patient settings.

The technical effect of the system and method of the present application is to provide a graphical user interface 57 that allows a user of a ventilator 54 to adjust the settings of the ventilator 54 by actually touching and moving portions of the various ventilator waveforms displayed on the ventilator 54 graphical user interface 57. This allows a user to visually adjust ventilator settings for a patient 52.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:
1. A ventilator system comprising:
   a ventilator operative to provide patient with ventilation;
   a ventilator display operative to provide a graphical user interface (GUI) wherein the GUI includes a touchscreen; and a processor programmed to:
  receive a selection for any of a mechanical or pressure supported ventilation (PSV) breath setting from the touchscreen;
  receive a selection for a target parameter and a control parameter for each of the mechanical or PSV breaths from the touchscreen;
  display on the ventilator display a set of known ideal waveforms corresponding to the selected breath setting, target parameter and control parameter;
  adjust the set of known ideal waveforms in response to altering any of the set of known ideal waveforms with the touchscreen to a desired patient setting; and
  set the ventilator according to the desired patient setting.

2. The system of claim 1, wherein the set of known ideal waveforms includes any of the following:
  a pressure waveform;
  a flow waveform; and
  a volume waveform.

3. The system of claim 2, wherein each of the pressure, flow and volume waveforms in the set of known ideal waveforms is displayed in a dedicated display area on the GUI.

4. The system of claim 1, wherein the GUI includes a plurality of adjustment points configured on the set of known ideal waveforms, such that a user may utilize the plurality of adjustment points to alter the set of known ideal waveforms with the touchscreen to the desired patient setting.

5. The system of claim 4, wherein placement of the plurality of adjustment points allows the user to adjust a set of parameters for each of the waveforms in the set of known ideal waveforms.

6. The system of claim 1, wherein the GUI further includes a confirm/cancel selector operable to provide the confirmation of the desired patient setting from the touchscreen.

7. The system of claim 1, wherein the GUI further includes a save/load selector operable to save the desired patient setting, and load a previously saved desired patient setting.

8. The system of claim 1, wherein the GUI further includes a show adjustment point selector operable to display all of the plurality of adjustment points on the GUI.

9. A computerized method of adjusting a ventilator system visually, comprising:
  providing a graphical user interface (GUI) on a ventilator display of a ventilator;
  selecting any of a mechanical breath or a pressure supported ventilation (PSV) breath setting using a touchscreen of the GUI;
  selecting a target parameter and a control parameter for each of the breath settings with the touchscreen of the GUI;
  displaying a set of known ideal waveforms on the GUI, said ideal waveforms corresponding to the selected breath setting, target parameter and control parameter;
  adjusting any of the set of known ideal waveforms with the GUI to a desired patient setting; and
  setting the ventilator with the GUI according to the desired patient setting.

10. The method of claim 9, wherein the set of known ideal waveforms includes any of the following:
  a pressure waveform;
  a flow waveform; and
  a volume waveform.

11. The method of claim 10, further comprising displaying each of the pressure, flow and volume waveforms in the set of known ideal waveforms in a dedicated display area on the GUI.

12. The method of claim 9, altering the set of known ideal waveforms with the touchscreen to the desired patient setting with a plurality of adjustment points configured on the set of known ideal waveforms.

13. The method of claim 12, further comprising a set of parameters for each of the waveforms in the set of known ideal waveforms with the plurality of adjustment points.

14. The method of claim 9, wherein the GUI further includes a confirm/cancel selector operable to provide the confirmation of the desired patient setting from the touchscreen.

15. The method of claim 9, wherein the GUI further includes a save/load selector operable to save the desired patient setting, and load a previously saved desired patient setting.

16. The system of claim 9, wherein the GUI further includes a show adjustment point selector operable to display all of the plurality of adjustment points on the GUI.

17. In a ventilator system having a graphical user interface (GUI) embodied on a ventilator display, a method of adjusting a ventilator visually, the method comprising:
  selecting with a touchscreen of the GUI any of a mechanical breath or pressure supported ventilation (PSV) breath setting;
  selecting with a touchscreen of the GUI a target parameter and a control parameter for each of the breath settings;
  displaying a set of known ideal waveforms on the ventilator display of the ventilator, said ideal waveforms corresponding to the selected breath setting, target parameter and control parameter;
  adjusting any of the set of known ideal waveforms to a desired patient setting; and
  setting the ventilator according to the desired patient setting.

18. The method of claim 17, wherein the GUI further includes a confirm/cancel selector operable to provide the confirmation of the desired patient setting from the touchscreen.

19. The method of claim 17, wherein the GUI further includes a save/load selector operable to save the desired patient setting, and load a previously saved desired patient setting.

20. The system of claim 17, wherein the GUI further includes a show adjustment point selector operable to display all of the plurality of adjustment points on the GUI.

* * * * *